US00PP27757P2

(12) United States Plant Patent
Stemkens

(10) Patent No.: US PP27,757 P2
(45) Date of Patent: Mar. 7, 2017

(54) ***VERBENA* PLANT NAMED 'VEAZ0017'**

(50) Latin Name: *Verbena hybrida*
Varietal Denomination: VEAZ0017

(71) Applicant: SYNGENTA CROP PROTECTION AG, Basel (CH)

(72) Inventor: Henricus Godefridus Wilhelmus Stemkens, Enkhuizen (NL)

(73) Assignee: Syngenta Participations AG, Basel (CH)

( * ) Notice: Subject to any disclaimer, the term of this patent is extended or adjusted under 35 U.S.C. 154(b) by 197 days.

(21) Appl. No.: 13/998,097

(22) Filed: Oct. 1, 2013

(30) Foreign Application Priority Data

Nov. 9, 2012 (CA) ..... 12-7792

(51) Int. Cl.
*A01H 5/02* (2006.01)

(52) U.S. Cl.
USPC ..... Plt./308

(58) Field of Classification Search
USPC ..... Plt./308
See application file for complete search history.

(56) References Cited

U.S. PATENT DOCUMENTS

PP19,467 P2 * 11/2008 Stemkens ..... Plt./308

OTHER PUBLICATIONS

Canadian Food Inspection Agency 2015, retrieved on May 26, 2015, retrieved from the Internet at <http://www.inspection.gc.ca/english/plaveg/pbrpov/cropreport/ver/app00009007e.shtml> pp. 1-4.*
Malmborg's 2012 Liner Availability, retrieved on May 26, 2015, retrieved from the Internet at <http://www.malmborgsinc.com/_ccLib/attachments/pages/availability1.4.12.pdf> one page.*

* cited by examiner

*Primary Examiner* — June Hwu
(74) *Attorney, Agent, or Firm* — Dale Skalla

(57) ABSTRACT

A new *Verbena* plant named 'VEAZ0017' particularly distinguished by the brilliant red-purple colored flowers with a small white-eye, deep green deeply lobed foliage, good branching with somewhat compact plant habit.

1 Drawing Sheet

Latin name of the genus and species of the plant claimed: *Verbena hybrida.*

Varietal denomination: 'VEAZ0017'.

BACKGROUND OF THE NEW PLANT

The present invention comprises a new *Verbena*, botanically known as *Verbena hybrida*, and hereinafter referred to by the variety name 'VEAZ0017'.

'VEAZ0017' is a product of a planned breeding program. The new cultivar has brilliant red-purple colored flowers with a small white eye, deep green deeply lobed foliage, good branching with somewhat compact plant habit.

'VEAZ0017' originated from a hybridization made in August 2007 in a greenhouse environment in Enkhuizen, The Netherlands. The female parent was the proprietary plant designated 'Puwydena', U.S. Plant Pat. No. 22,535, with reddish flowers, a plant habit with fewer branches and higher seed set rate than that of 'VEAZ0017'.

The male parent of 'VEAZ0017' was a proprietary plant designated 'Flagdena', U.S. Plant Pat. No. 22,438, with pink bicolored flowers, much more vigorous habit and a higher seed set rate than that of 'VEAZ0017'. The seed was sown in February 2008 in a greenhouse environment in Enkuizen, The Netherlands.

'VEAZ0017' was selected as one flowering plant within the progeny of the stated cross in August 2008 in a greenhouse environment in Enkhuizen, The Netherlands. The first act of asexual reproduction of 'VEAZ0017' was accomplished when vegetative stem cuttings were propagated from the initial selection in August 2008 in a greenhouse environment in Enkhuizen, The Netherlands.

BRIEF SUMMARY OF INVENTION

Horticultural examination of plants grown from cuttings of the plant initiated in August 2008 in Enkhuizen, The Netherlands, and continuing thereafter, has demonstrated that the combination of characteristics as herein disclosed for 'VEAZ0017' are firmly fixed and are retained through successive generations of asexual reproduction.

'VEAZ0017' has not been observed under all possible environmental conditions. The phenotype may vary significantly with variations in environment such as temperature, light intensity, and day length.

Plant Breeder's Rights for this cultivar were applied for in Canada on Nov. 9, 2012, No. 12-7792 and at the Community Plant Variety Office on Sep. 25, 2012, No. 2012-2026. 'VEAZ0017' has not been made publicly available more than one year prior to the filing of this application.

The following traits have been repeatedly observed and are determined to be basic characteristics of the new variety. The combination of these characteristics distinguishes this *Verbena* as a new and distinct variety.

BRIEF DESCRIPTION OF THE PHOTOGRAPHS

The accompanying photographic drawing shows typical flower and foliage characteristics of 'VEAZ0017' with colors being as true as possible with an illustration of this type.

Figure 1:
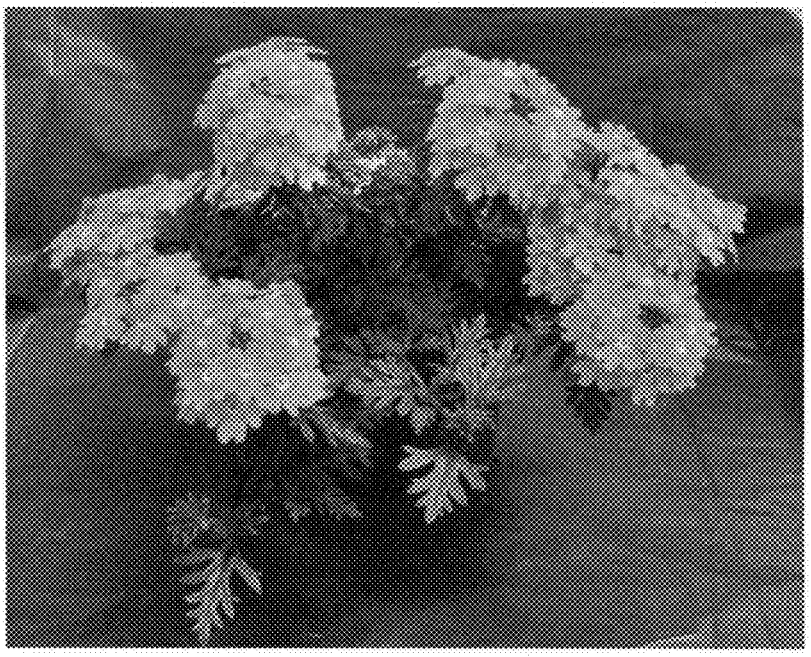
Figure 2:
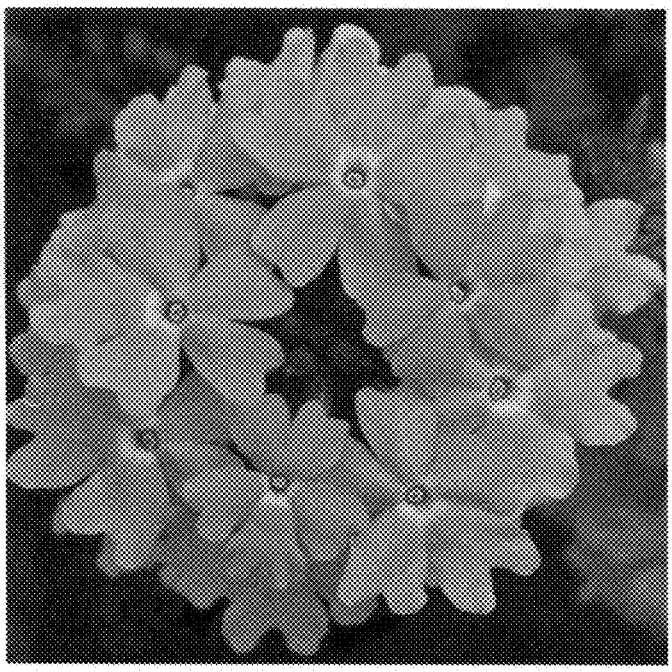

The photographic drawing shows in FIG. 1 a flowering plant of the new variety and in FIG. 2 a close-up of the inflorescences.

DETAILED BOTANICAL DESCRIPTION

The plant descriptions and measurements were taken in Enkhuzien, The Netherlands in August from plants growing in an outdoors trial in one (1) meter window boxes with each box containing 5 plants. These plants used were about 5 months old.

The aforementioned photographs were taken in Andijk, The Netherlands in May from plants growing in a greenhouse trial in 12 cm pots. These plants used were about 9-11 weeks old with no terminal pinches to the plants.

Color references are made to The Royal Horticultural Society Colour Chart (R.H.S.) 2001.

TABLE 1

DIFFERENCES BETWEEN THE NEW VARIETY 'VEAZ0017' AND A MOST SIMILAR VARIETY

| | 'VEAZ0017' | 'Carmali' (U.S. Plant Pat. No. 19,467) |
|---|---|---|
| Flower color: | Slightly more blueish hue | Slightly more carmine |
| Flower fading | Color fades more | Color fades less |
| Flower size: | Larger | Smaller |
| Plant habit: | Bigger/wider | Smaller |
| Length of peduncles: | Shorter | Longer |

Plant:

*Form, growth and habit.*—Herbaceous; mounding and outwardly spreading growth habit; bushy and tight habit with relatively short branches, and long peduncles.

*Plant height.*—13-15.0 cm.

*Plant height (inflorescence included).*—15-17.0 cm.

*Plant width.*—About 40-46.0 cm.

Roots:

*Number of days to initiate and produce roots.*—About 10-14 days at about 22 degrees C.

*Type.*—Fine, fibrous, free branching.

*Color.*—RHS N155B but whiter.

Foliage:

*Arrangement.*—Alternate, simple.

*Immature, leaf color, upper surface.*—Closest to RHS 143A.

*Immature, leaf color, lower surface.*—Between RHS138B and RHS 143A.

*Mature, leaf color, upper surface.*—RHS 137A to RHS 137B.

*Mature, leaf color, lower surface.*—Closest to RHS 138B.

*Length.*—2.9-3.9 cm.

*Width.*—2.3-2.6 cm.

*Shape.*—Ovate.

*Base shape.*—Attenuate.

*Apex shape.*—Acute.

*Margin.*—Serrated, and sometimes deeply and irregularly incised.

*Texture, upper surface.*—Appears almost glabrous.

*Texture, lower surface.*—Pilose, few glandular hairs mostly on the mid-veins.

*Color of veins, upper surface.*—RHS 144C basally, otherwise indistinct.

*Color of veins, lower surface.*—RHS 145C basally, otherwise indistinct.

*Pattern of veining.*—Pinnate.

*Petioles color, upper surface.*—RHS 144C.

*Petioles color, lower surface.*—RHS 145C.

*Petioles length.*—0.2-0.4 cm.

*Petiole width.*—0.2-0.3 cm.

*Texture.*—Weakly pilose.

Stem:

*Quantity of main branches per plant.*—20-30.0 cm.

*Color of stem.*—Some are RHS 143C, others RHS 144A.

*Stem length.*—About 15-17.0 cm.

*Stem width.*—0.25-0.3 cm.

*Length of internodes.*—1.5-3.0 cm.

*Texture.*—Hirtellous, short hairs.

*Color of peduncle.*—RHS 147A with some having a weak overlay of anthocyanins of about RHS 200C.

*Length of peduncle.*—Mostly 2.0-4.5 cm, some are close to 7.0 cm at a more mature stage.

*Peduncle diameter.*—0.2 cm.

*Texture.*—Pilose, glandular hairs.

Inflorescence:

*Type.*—Terminal, umbel-like, but actually a spike, umbrella-shaped.

*Blooming habit.*—Flowers continuously.

*Lastingness of individual blooms on the plant.*—About 6 days in the greenhouse and depending on cultural and environmental conditions.

*Fragrance.*—None.

*Number of inflorescences per plant.*—About 30-40 at various stages.

*Horizontal diameter of inflorescence.*—4.5-5.0 cm.

*Depth of inflorescence.*—1.9-2.1 cm.

*Number of florets per inflorescence (including any buds at the time).*—About 25-30.

Bud (just when opening/showing color):

*Color.*—RHS 63A.

*Length.*—1.2 cm.

*Width.*—0.3-0.4 cm.

*Shape.*—Tubular with bulbous end.

Corolla:

*Form.*—Sessile; salverform, composed of 5 partly fused petals with a base of a narrow tube.

*Immature color, upper surface.*—RHS N57A but a deeper hue.

*Immature color, lower surface.*—RHS N57C.

*Mature color, upper surface.*—RHS N57B with a small eye of RHS 69D or RHS N155D.

*Mature color, lower surface.*—Between RHS N57B and RHS N57C.

*Floret diameter.*—1.5-1.7 cm.

*Floret length (depth).*—About 1.0-1.1 cm.

*Petal length.*—0.8-0.9 cm.

*Petal width.*—0.5-0.7 cm.

*Shape.*—Obovate.

*Apex shape.*—Emarginate to retuse with some just rounded.

*Margin.*—Entire.

*Petal texture, upper surface.*—Papillose.

*Petal texture, lower surface.*—Papillose.

*Corolla tube color inside.*—Weakly RHS 75C.

*Corolla tube color outside.*—RHS 63C at corolla end and RHS 145D at lower half of tube.

*Corolla tube length.*—1.4 cm.

*Corolla tube width.*—0.2 cm.
*Corolla texture, inside.*—Papillose with hairs at the corolla flare.
*Corolla texture, outside.*—Papillose.
*Throat hair color.*—Closest to RHS N74D.

Calyx:
*Type.*—Five sepals whose margins are fused to each other along their length, with a transparent membrane of less than 0.1 cm in width and with one smaller sepal attached to the base of the calyx.
*Color of sepals.*—RHS 147B with a bit of RHS 183A at the upper margins.
*Length of sepals.*—0.8-0.9 cm.
*Width of sepals.*—0.2 cm.
*Sepal shape.*—Linear.
*Apex shape.*—Acute.
*Margins.*—Entire, where not fused.
*Texture, upper surface.*—Glabrous.
*Texture, lower surface.*—Pilose, glandular hairs.

Reproductive organs:
*Gynoecium.*—
*Pistil.*—1.
*Pistil length.*—2.0-2.2 cm.
*Style color.*—RHS 144D.
*Style length.*—1.7-1.8 cm.
*Stigma color.*—RHS 144C.
*Stigma shape.*—Bi-lobed or bi-parted.
*Ovary color.*—RHS 144C.
*Ovary length.*—0.15 cm.
*Ovary width.*—0.1 cm.
*Androecium.*—
*Stamens.*—Anthers and filaments fused to upper half of corolla tube; four anthers with two pollen sacs per anther.
*Color of filaments.*—RHS 149D.
*Filament length.*—0.2 cm.
*Anther color.*—RHS 145C.
*Anther length.*—0.1 cm.
*Color of pollen.*—RHS 145D.
*Pollen amount.*—Sparse.

Fertility/seed set: Has not been observed to date.
Disease/pest resistance: Has not been observed to date.

What is claimed is:

1. A new and distinct variety of *Verbena* plant named 'VEAZ0017' substantially as illustrated and described herein.

* * * * *